United States Patent [19]

Illig et al.

[11] Patent Number: 5,352,434
[45] Date of Patent: Oct. 4, 1994

[54] X-RAY CONTRAST COMPOSITIONS CONTAINING A BARIUM SALT AND FILM-FORMING MATERIALS

[75] Inventors: Carl B. Illig, Phoenixville; John L. Toner, Downingtown, both of Pa.

[73] Assignee: Sterling Winthrop Inc., Malvern, Pa.

[21] Appl. No.: 104,222

[22] Filed: Aug. 9, 1993

Related U.S. Application Data

[63] Continuation-in-part of Ser. No. 938,786, Sep. 1, 1992, abandoned, which is a continuation-in-part of Ser. No. 877,690, May 1, 1992, abandoned.

[51] Int. Cl.$^5$ .................. A61K 49/04; A61K 33/04; A61K 31/715
[52] U.S. Cl. ............................. 424/4; 424/709; 514/54; 514/57; 514/941; 514/942
[58] Field of Search ............... 424/4, 5, 709; 514/54, 514/57, 941, 942

[56] References Cited

U.S. PATENT DOCUMENTS

| | | | |
|---|---|---|---|
| 2,659,690 | 6/1950 | Slaybaugh | 167/95 |
| 2,680,089 | 6/1954 | Lowy | 167/95 |
| 2,832,722 | 8/1958 | Singher | 167/95 |
| 3,192,118 | 6/1965 | Battista et al. | 167/95 |
| 4,038,379 | 7/1977 | Elinov et al. | 424/4 |
| 4,069,306 | 1/1978 | Rothman | 424/4 |
| 4,120,946 | 10/1978 | Queille et al. | 424/4 |
| 4,588,574 | 5/1986 | Felder et al. | 423/554 |
| 5,019,370 | 5/1991 | Jay et al. | 424/4 |

FOREIGN PATENT DOCUMENTS 55-127322 10/1980 Japan .

OTHER PUBLICATIONS

Wang et al., Yaoxne Xuebao, vol. 16, No. 8:610–617 (1981).
James et al., Pharm. Acta. Helvetiae, 47, 244–256 (1972).

*Primary Examiner*—Gary E. Hollinden
*Attorney, Agent, or Firm*—Arthur Rosenstein; Imre Balogh

[57] ABSTRACT

Disclosed are x-ray contrast compositions for oral or retrograde examination of the gastrointestinal tract comprising a polymeric material capable of forming a coating on the gastrointestinal tract and a barium salt in a pharmaceutically acceptable carrier; and methods for their use in diagnostic radiology of the gastrointestinal tract.

4 Claims, No Drawings

X-RAY CONTRAST COMPOSITIONS CONTAINING A BARIUM SALT AND FILM-FORMING MATERIALS

This is a continuation-in-part of application Ser. No. 07/938,786 filed on Sep. 1, 1992, abandoned, which, in turn, is a continuation-in-part of application Ser. No. 07/877,690 filed on May 1, 1992, abandoned.

BACKGROUND OF THE INVENTION

1. Field of the Invention

This invention relates to an x-ray contrast composition for oral or retrograde administration to a mammal comprising a barium salt; as the contrast producing agent and a polymeric film-forming material.

2. Reported Developments

Roentgenographic examination utilizing x-rays and computed tomography (hereinafter CT) scans of fractures and other conditions associated with the skeletal system is routinely practiced without the use of contrast agents. X-ray visualization of organs containing soft tissue, such as the gastrointestinal (hereinafter GI) tract, requires the use of contrast agents which attenuate x-ray radiation. D. P. Swanson et al in "Pharmaceuticals In Medical Imaging", 1990, MacMillan Publishing Company, provides an excellent background in medical imaging utilizing contrast agents and compositions therewith.

The desiderata for an ideal GI contrast agent includes: good toxicological profile; the ability to fill the entire bowel/lumen and evenly coat the gut mucosa so that the presence of the bowel is detectable when the lumen is not distended; palatability and nonirritation to the intestinal mucosa; and passing through the GI tract without producing artifacts or stimulating vigorous intestinal peristalsis.

The most widely used contrast agents for the visualization of the GI tract is barium sulfate administered as a suspension orally or rectally as an enema. (See for example, U.S. Pat. Nos. 2,659,690; 2,680,089; 3,216,900; 3,235,462; 4,038,379 and 4,120,946) Notwithstanding its relatively good contrast characteristics, negligible absorption from the GI tract following oral or rectal administration and speedy excretion from the body, barium sulfate has certain disadvantages. In the presence of intestinal fluids, it lacks homogeneity which can result in poor x-ray images. In the colon, when administered as an enema, it flocculates and forms irregular clumps with fecal matter. The prior art considers as a serious problem the difficulty in achieving uniform adherence to, and coating of, the mucosa of the GI tract by the water insoluble barium sulfate to provide high quality x-ray photographs. As a result of inadequate adherence to, and non-uniform coating of the mucosa, the x-ray results are often inferior, misleading to the practitioner and the imaging process must be repeated. It has also been observed that the barium sulfate, and other solid inorganic particulate radiopaque agents tend to settle out in the patient after evacuation but before and during x-ray imaging, which again deleteriously affects the quality of the x-ray pictures.

These drawbacks were addressed by many investigators and their efforts resulted in great improvements over the years. The drawbacks of uneven coating of the mucosa by an x-ray contrast composition and insufficient adherence to the mucosa proved to be rather difficult to solve. To that end, the use of certain polymer additives were proposed as illustrated hereunder.

U.S. Pat. No. 4,069,306 discloses an x-ray contrast preparation which is said to adhere to the walls of body cavities. The preparation comprises a finely divided water-insoluble inorganic x-ray contrast agent and minute particles of a hydrophilic polymer which is insoluble in water but is water-swellable. The body cavity is supplied with such preparation suspended in water. The x-ray contrast agent is present in admixture with and/or enclosed in and/or adhered to said minute polymer particles.

U.S. Pat. No. 4,120,946 discloses a pharmaceutical composition for barium opacification of the digestive tract, comprising colloidal barium sulfate and a polyacrylamide in an aqueous vehicle. The polyacrylamide forms a viscous solution at low concentration which makes it possible to maintain the barium sulfate in suspension and at the same time permit good adherence of the preparation to the walls of the organ which it desired to x-ray.

U.S. Pat. No. 5,019,370 discloses a biodegradable radiographic contrast medium comprising biodegradable polymeric spheres which carry a radiographically opaque element, such as iodine, bromine, samarium and erbium. The contrast medium is provided either in a dry or liquid state and may be administered intravenously, orally and intra-arterially.

Japanese Patent Application No. 55-127322 discloses x-ray contrast compositions containing barium sulfate and a polymeric substance selected from carboxymethyl cellulose salts, propylene glycol alginate, cellulose sulfate polyacrylate, pectin and tragacanth gum. The polymeric substance is used to increase the viscosity of the compositions.

While these polymeric materials enhance attachment of the contrast agent used therewith to the walls of organs for better visualization thereof, they do not provide a polymeric coating thereon. As such, there is still a need for an improved x-ray imaging medium that uniformly coats the soft tissues subjected to diagnostic x-ray examination.

We have now discovered that good adherence to, and uniform coating of the mucosa of the intestine can be obtained by a barium salt in combination with a film-forming material to provide high quality x-ray results.

SUMMARY OF THE INVENTION

It is the object of the present invention to provide compositions for coating the gastrointestinal tract of mammals to form an effective radiopaque coating thereon by which diagnostic examination of the GI tract may be accomplished. To that end, a thin coating is formed on the inner surface of the GI tract effected by ingesting, prior to visualization by an x-ray emitting device, a polymeric film former, which has incorporated therein a barium salt, capable of coating the GI tract. The removal of the coating from the inner surface of the GI tract occurs as a result of the normal turnover of cells, that is, within about 24 to 48 hours. Such compositions must meet several requirements: the film former must be nontoxic; must not contain leachable or digestible components that would deleteriously affect the patient; no components of the coating should be absorbed by, and pass through, the inner surface of the intestine; and the composition must be capable of forming a film in the pH range of from about 5 to about 8.

The object of the present invention is achieved by a composition comprising: a barium salt; a polymeric material which is at least partially water soluble and contains polarizable or ionizable groups; and a divalent metal ion selected from the group consisting of $Mg^{++}$, $Ca^{++}$, $Zn^{++}$ and $Ba^{++}$ which potentiates the effect of the polymeric material as a film former on the mucosa of the GI tract.

The barium salt, the polymeric film former and the divalent metal ion are incorporated in a solid or liquid media for administration to a mammal for x-ray visualization of the GI tract.

The preferred x-ray contrast agent utilized in the present invention is barium sulfate which is a white, radiopaque, crystalline powder that is essentially insoluble in water. It is commercially available in the particle size range of 0.001 to 0.1 micron diameter. However, good results are obtainable with other finely-divided, inorganic, essentially water-insoluble salts of barium including barium hexaboride, barium chromite, barium fluogallate, barium tri-ortho phosphate, barium metasilicate, barium titanate, barium zirconate and zirconium oxide. The compositions of the present invention contain from about 5% w/w to about 95% w/w of the barium salt. The compositions may be in the form of solids, dispersions, colloids or suspensoids, however, we prefer to use colloids as the preferred embodiment.

The gist of the present invention resides in an x-ray contrast composition designed for depositing a thin, flexible film membrane onto the mucosal lining of the nutrient absorbing inner surface of the intestine of a patient to form a barrier between the nutrient absorbing inner surface and the content of the intestine, the flexible film membrane to remain bound to the mucosal lining until eliminated by normal cell turnover comprising based on w/w: of from about 0.001 to about 25% of a polymeric material capable of forming a film membrane on the gastrointestinal tract in the pH range of from about 5 to about 8, the polymeric material is selected from the group consisting of anionic polymers carrying negative charges in the ionized form, cationic polymers carrying positive charges in the ionized form and neutral polymers having polarizable electrons selected from the group consisting of oxygen, nitrogen, sulfur, fluoride, chloride, bromide and iodide in combination with of from about 0.001 to about 20% of a divalent cation to potentiate the binding of the flexible film membrane to the mucosal lining selected from the group consisting of $Ca^{++}$, $Mg^{++}$, $Zn^{++}$ and $Ba^{++}$; and of from about 5 to about 95% of a barium salt in a pharmaceutically acceptable carrier.

DETAILED DESCRIPTION OF THE INVENTION

Starting materials, reagents and solvents can be obtained from chemical suppliers, such as Aldrich, Baker and Eastman Chemical Companies; alternatively, they may be prepared by techniques known in the prior art.

The polymers that were found to be suitable for forming a thin coating on the GI tract can be classified as anionic, cationic and neutral polymers, a description of which follows. U.S. Pat. No. 4,623,539, the disclosure of which is incorporated by reference, pertains to such polymers.

The barium salt is incorporated in the polymeric material along with the divalent cation by any suitable techniques, such as by mixing, blending, precipitating or by enclosing the contrast agent into minute polymeric particles.

The barium salt, polymeric material and divalent cation blend is then formulated for administration using physiologically acceptable carriers or excipients in a manner within the skill of the art. The barium salt, with the addition of pharmaceutically acceptable aids (such as surfactants and emulsifiers) and excipients, may be suspended in an aqueous medium resulting in a dispersion, suspension or colloid. Alternatively, the barium salt, polymeric material and divalent cation may be formulated into a solid form, such as tablets or capsules.

Solid compositions of the present invention shall contain, instead of surfactants/emulsifiers and water used in the liquid compositions, bulking agents and other pharmaceutically acceptable ingredients advantageously employed to render the compositions palatable.

When the x-ray composition is formulated as a tablet, the bulking agent should have good compression characteristics. Suitable bulking agents are well known in the art and include a sweetener such as sugars. e.g. sucrose, and polyhydric alcohols, e.g. mannitol, sorbitol and xylitol, and mixtures thereof. When formulated as a tablet, it is preferable to incorporate in the composition one or more tablet lubricating agents, such as stearic acid, magnesium stearate and talc. The amount of the tablet lubricating agents as well as any other ingredients required to easily prepare the solid compositions, can readily be determined by the skilled formulator. The solid compositions may have incorporated therein optional pharmaceutically acceptable ingredients in order to impart thereto additional desirable properties, such as flavorants and colorants.

Compositions

Liquid compositions of the present invention comprise the following pharmaceutically acceptable components based on % w/w:

| Polymeric Material | 0.001–25 |
| --- | --- |
| Divalent Cation | 0.001–20 |
| Barium Salt | 5–95 |
| Excipient | 0–20 |
| Aids (Surfactants/Emulsifiers) | 0.01–20 |
| Water | q.s. to 100 |

Solid compositions of the present invention comprise the following pharmaceutically acceptable components based on % w/w:

| Polymeric Material | 0.001–25 |
| --- | --- |
| Divalent Cation | 0.001–20 |
| Barium Salt | 5–95 |
| Balking Agent/Lubricant/Flavor | q.s. to 100 |

Excipients advantageously used in the formulations include viscosity mediating and stabilizing agents, such as microcrystalline cellulose, ethylcellulose, hydroxypropyl methylcellulose and gum arabic. Physiologically acceptable substances may also be included, such as sodium citrate, sodium chloride, therapeutic substances, antacid substances and flavoring agents. The inclusion of antimicrobial/antiseptic agents such as methyl parahydroxybenzoate, ethyl parahydroxybenzoate, propyl parahydroxy-benzoate, benzoic acid, benzyl alcohol, phenol, sodium benzoate, EDTA or sorbic acid may also be desirable in some formulations.

Surfactants or emulsifiers can be used alone or in combination with other emulsifying agents and surfactants. For example, Dow Corning Medical Antifoam AF, which is a composition of 30% w/v polydimethylsiloxane and silica aerogel, 14% w/v stearate emulsifiers and 0.075% w/v sorbic acid, the balance being water, may be used by itself. Intralipid, which is an emulsion of fatty acids needs the presence of a suspending agent for it to form an acceptable emulsion with contrast agents of the present invention. The amount of such surfactants may be in the range of from 0.01 to 20% w/w of the aqueous formulations, although the amount, in general, is kept as low as possible, preferably in the range of 0.05 to 5% w/w. The surface active agents may be cationic, anionic, nonionic, zwitterionic or a mixture of two or more of these agents.

Suitable cationic surfactants include cetyl trimethyl ammonium bromide. Suitable anionic agents include sodium lauryl sulphate, sodium heptadecyl sulphate, alkyl benzenesulphonic acids and salts thereof, sodium butylnapthalene sulfonate, and sulphosuccinates. Zwitterionic surface active agents are substances that when dissolved in water they behave as diprotic acids and, as they ionize, they behave both as a weak base and a weak acid. Since the two charges on the molecule balance each other out they act as neutral molecules. The pH at which the zwitterion concentration is maximum is known as the isoelectric point. Compounds, such as certain amino acids having an isoelectric point at the desired pH of the formulations of the present invention are useful in practicing the present invention.

In preparing the formulations of the present invention we prefer to use nonionic emulsifiers or surface active agents which, similarly to the nonionic contrast agents, possess a superior toxicological profile to that of anionic, cationic or zwitterionic agents. In the nonionic emulsifying agents the proportions of hydrophilic and hydrophobic groups are about evenly balanced. They differ from anionic and cationic surfactants by the absence of charge on the molecule and, for that reason, are generally less irritant than the cationic or anionic surfactants. Nonionic surfactants include carboxylic esters, carboxylic amides, ethoxylated alkylphenols and ethoxylated aliphatic alcohols.

One particular type of carboxylic ester nonionic surface active agents are the partial, for example mono-, esters formed by the reaction of fatty and resin acids, for example of about 8 to about 18 carbon atones, with polyalcohols, for example glycerol, glycols such as mono-, di-, tetra- and hexaethylene glycol, sorbitan, and the like; and similar compounds formed by the direct addition of varying molar ratios of ethylene oxide to the hydroxy group of fatty acids.

Another type of carboxylic esters is the condensation products of fatty and resin partial acids, for example mono-, esters ethylene oxide, such as fatty or resin acid esters of polyoxyethylene sorbitan and sorbitol, for example polyoxyethylene sorbitan, mono-tall oil esters. These may contain, for example, from about 3 to about 80 oxyethylene units per molecule and fatty or resin acid groups of from about 8 to about 18 carbon atoms. Examples of naturally occurring fatty acid mixtures which may be used are those from coconut oil and tallow while examples of single fatty acids are dodecanoic acid and oleic acid.

Carboxylic amide nonionic surface active agents are the ammonia, monoethylamine and diethylamides of fatty acids having an acyl chain of from about 8 to about 18 carbon atoms.

The ethoxylated alkylphenol nonionic surface active agents include various polyethylene oxide condensates of alkylphenols, especially the condensation products of mono-alkylphenols or dialkylphenols wherein the alkyl group contains about 6 to about 12 carbon atoms in either branched chain or particularly straight chain configuration, for example octyl cresol, octyl phenol or nonyl phenol, with ethylene oxide, said ethylene oxide being present in amounts equal to from about 5 to about 25 moles ethylene oxide per mole of alkylphenol.

Ethoxylated aliphatic alcohol nonionic surface active agents include the condensation products of aliphatic alcohols having from about 8 to 18 carbon atoms in either straight chain or branched chain configuration, for example oleyl or cetyl alcohol, with ethylene oxide, said ethylene oxide being present in equal amounts from about 30 to about 60 moles of ethylene oxide per mole of alcohol.

Preferred nonionic surface active agents include:
(a) Sorbitan esters (sold under the trade name Span) having the formula:

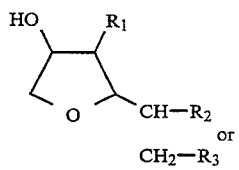

wherein
$R_1 = R_2 = OH$, $R_3 = R$ for sorbitan monoesters,
$R_1 = OH$, $R_2 = R_3 = R$ for sorbitan diesters,
$R_1 = R_2 = R_3 = R$ for sorbitan triesters,
where $R = (C_{11}H_{23})COO$ for laurate, $(C_{17}H_{33})COO$ for oleate, $(C_{15}H_{31})COO$ for palmitate, $(C_{17}H_{35})COO$ for stearate;
(b) Polyoxyethylene alkyl ethers (i.e. Brijs) having the formula:

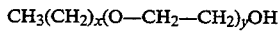

where (x+1) is the number of carbon atoms in the alkyl chain, typically:
12 lauryl (dodecyl)
14 myristyl (tetradecyl)
16 cetyl (hexadecyl)
18 stearyl (octadecyl)
and y is the number of ethylene oxide groups in the hydrophilic chain, typically 10–60;
(c) Polyoxyethylene sorbitan fatty acid esters, sold under the trade names of Polysorbates 20, 40, 60, 65, 80 & 85; and
(d) Polyoxyethylene stearates, such as:
poly(oxy-1.2-ethanediyl), α-hydro-ω-hydroxyoctadecanoate;
polyethylene glycol monostearate; and
poly(oxy-1,2-ethanediyl)-α-(1-oxooctadecyl)-ω-hydroxypolyethylene glycol monostearate.

The film former polymeric materials used in accordance with the present invention include anionic polymers, cationic polymers and neutral polymers.

I. Anionic Polymers

The anionic polymers carry negative charges in the ionized form and are capable of binding to cell surfaces mainly by electrostatic forces. Suitable anionic polymers include the following:

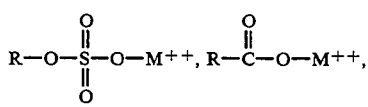

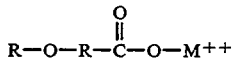

wherein
R is the polymeric chain;

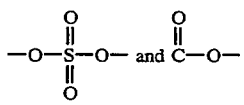

are anionic ligands; and
$M^{++}$ is a divalent cation.

Specific artionic polymers useful in the practice of the present invention include:
(1) Sulfated polysaccharides of the formula:

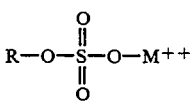

wherein R is

| | |
|---|---|
| 3,6-anhydro-D-galactose linked through C-4 to D-galactose; | (kappa carrageenan) |
| α-D-galactose units (1-3) linked; D-galactose | (lambda carrageenan) (iota carrageenan) |
| 3,6-anhydro-D-galactose; D-galactose | (Agar - Agar) |
| 3,6-anhydro-L-galactose: D-galactose | (Furcellaren) |
| 3,6-anhydro-D-galactose; D-glucopyranose; | (Laminarin sulfate) |
| Galactan; and | (Galactan sulfate) |
| Galactosamino-glucuronans and | (Chondroitin sulfates); |

$M^{++}$ is $Mg^{++}$, $Ca^{++}$, $Zn^{++}$, $Ba^{++}$ or mixtures thereof.

(2) Carboxylated polysaccharides of the formula:

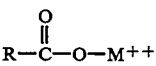

wherein R is D-galacturonoglycan; and (Pectin) anhydro-D-mannuronic acid and anhydro-L-guluronic acid (Algin) residues; and
$M^{++}$ is $Mg^{++}$, $Ca^{++}$, $Zn^{++}$, $Ba^{++}$ or mixtures thereof.

(3) Cellulose derivatives of the formulae:

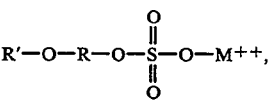

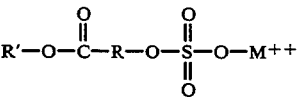

and

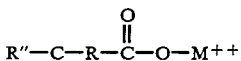

wherein R is an anhydroglucose residue;
R' is $CH_3$, $C_2H_5$ or $C_3H_7$;
R'' is $CH_3$ or $C_2H_5$; and
$M^{++}$ is $Mg^{++}$, $Ca^{++}$, $Zn^{++}$, $Ba^{++}$ or mixtures thereof.

Examples of cellulose derivatives include: sodium ethylcellulose sulfate, sodium cellulose acetate sulfate and sodium carboxymethyl cellulose.

(4) Sulfated, sulfonated or carboxylated synthetic polymers of the formula:

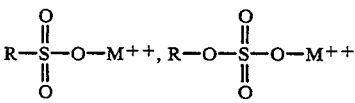

and

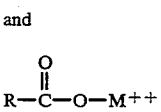

wherein
R is an aliphatic or aromatic hydrocarbon, such as polystyrene, poly(sulfon) resin or carboxylated (poly) vinyl; and
$M^{++}$ is $Mg^{++}$, $Ca^{++}$, $Zn^{++}$, $Ba^{++}$ or mixtures thereof.

II Cationic Polymers

The cationic polymers carry positive charges in the ionized form. Suitable polymers for practicing the present invention include: dermatan sulfate, keratosulfate, hyaluronic acid, heparin and chitin.

III Neutral Polymers

Neutral polymers having polarizable electrons such as oxygen, nitrogen, sulfur, fluoride, chloride, bromide and iodide are also suitable for practicing the present invention. In the presence of a cation, such as $Mg^{++}$, $Ca^{++}$, $Zn^{++}$ or $Ba^{++}$, the polymers are partially polarized thereby providing intermolecular interactions between the polymer and the intestinal wall. Examples of these polymers include:

(a) Polysaccharides, such as starch, glycogen, glucan, fructans, mannans, galactomannas, glucomannans, galactans, xylans, glycuranans, dextran and starch amylose;

(b) Cellulose derivatives, such as methylcellulose, hydroxyethylcellulose, ethylhydroxyethyl cellulose, hydroxypropyl methylcellulose and hydroxypropyl cellulose; and (c) Synthetic polymers, such as polyvinylpyrrolidone, polyvinyl alcohol and ethylene oxide polymers.

Exemplary formulations of the present invention are as shown:

| Example 1 | |
|---|---|
| Barium Sulfate (114 mg Ba/ml) | 1.94 g (19.4% w/v) |
| Dow Corning Med. Antifoam AF emulsion | 3.50 g (35% w/v) |
| Galactan sulfate | 0.5 g (5% w/v) |
| Calcium lactate | 0.5 g (5% w/v) |
| Purified Water | q. s. to 10 ml |

-continued

Example 2

| | |
|---|---|
| Barium Titanate (114 mg Ba/ml) | 1.94 g (19.4% w/v) |
| Safflower Oil | 2.00 g (20% w/v) |
| Tween-21 | 0.25 g (2.5% w/v) |
| Hydroxypropyl methylcellulose (4,000 cPs) | 2.50 g of 2% solution |
| Calcium lactate | 0.2 g (2% w/v) |
| Purified Water | q. s. to 10 ml |

Example 3

| | |
|---|---|
| Barium Hexaboride (114 mg Ba/ml) | 1.68 g (16.8% w/v) |
| Mineral Oil | 0.50 g (5% w/v) |
| Heparin | 0.25 g (2.5% w/v) |
| Tween-21 | 0.25 g (2.5% w/v) |
| Calcium lactate | 0.25 g (2.5% w/v) |
| Purified Water | q. s. to 10 ml |

Example 4

| | |
|---|---|
| Barium Tri-ortho-phosphate (114 mg Ba/ml) | 1.67 g (16.7% w/v) |
| Simplesse 100 (Nutrasweet Co.) | 3.00 g (30% w/v) |
| Calcium lactate | ~0.5 (5% w/v) |
| Hydroxypropyl methylcellulose (4000 cPs) | 2.50 g of 2% solution |
| Purified Water | q. s. to 10 ml |

The compositions of the invention may be administered orally to the patient for radiological examination of the GI tract. The compositions of the invention may also be administered rectally in the form of enemas to a patient for radiologic examination of the colon.

The dosages of the contrast agent used according to the method of the present invention will vary according to the precise nature of the ingredients used. Preferably, however, the dosage should be kept as low as is consistent with achieving contrast enhanced imaging. By employing as small amount of the composition as possible, toxicity potential is minimized. For most formulations of the present invention dosage will be in the range of from about 0.1 to about 20.0 g Ba/kg body weight, preferably in the range of from about 0.4 to about 8.0 g Ba/kg of body weight, and most preferably, in the range of from about 1.0 to about 3.0 g Ba/kg body weight for regular x-ray visualization of the GI tract. For CT scanning the contrast agents of the present invention will be in the range of from about 1 to about 800 mg Ba/kg body weight, preferably in the range of from about 15 to about 250 mg Ba/kg body weight, and most preferably in the range of from about 35 to about 90 mg Ba/kg body weight.

The concentration of the contrast agent should be in the range of from about 5% w/w to about 95% w/w of the formulation, preferably from about 10% w/w to about 60% w/w and most preferably of from about 15% w/w to about 40% w/w.

The concentration of the film forming polymeric material depends on the particular polymer used, however, it should be in the range of 0.001 to about 25% w/w or higher in combination with a divalent substance, such as calcium lactate, having a concentration range of 0.001 to 20% w/w. The use of less than about 0.001% of a divalent cation was found less than satisfactory in forming a film on the mucosa of the intestines. Dosage level of the polymeric material may be in the range of from about 2 to about 20 g/kg body weight or higher.

The compositions of the present invention possess very good adherence to the walls of the gastrointestinal tract by forming an essentially uniform coating thereon.

The invention, having been fully described, it will be apparent to one skilled in the art that changes and modifications can be made thereto without departing from the spirit and scope thereof.

What is claimed is:

1. Am x-ray contrast composition designed for depositing a thin, flexible film membrane onto the mucosal lining of the nutrient absorbing inner surface of the intestine to form a barrier between the nutrient absorbing inner surface and the content of the intestine, the flexible film membrane to remain bound to the mucosal lining until eliminated by normal cell turnover comprising based on w/w:
   (a) of from about 0.001 to about 25% of a polymeric material capable of forming a film membrane on the gastrointestinal tract in the pH range of from about 5 to about 8, said the polymeric material being selected from the group consisting of:
   dermatan sulfate,
   hepatosulfate,
   hyabromic acid,
   heparin,
   chitin, and
   ethylene oxide:
   (b) of from about 0.1 to about 20% of a divalent cation to potentiate the binding of the flexible film membrane to the mucosal lining selected from the group consisting of $Ca^{++}$, $Mg^{++}$, $Zn^{++}$ and $Ba^{++}$;
   (c) of from about 5 to about 95% of a barium salt in a liquid pharmaceutically acceptable carrier comprising a surfactant selected from the group consisting of
   cetyltrimethyl ammonium bromide,
   dodecyl ammonium bromide,
   sodium lauryl sulfate:
   sodium heptadecyl sulfate,
   alkyl benzene sulfonic acid,
   carboxylic esters,
   carboxylic amides,
   ethoxylated alkylphenols,
   ethoxylated aliphatic alcohols,
   polyoxyethylene alkyl ethers
   polyoxyethylene sorbitan fatty acid esters; and
   zwitterionic surfactants.

2. The x-ray contrast composition of claim 1 wherein said barium salt is selected from the group consisting of barium sulfate, barium hexaboride, barium chromite, barium fluogallate, barium tri-orthophosphate, barium metasilicate, barium titanate, and barium zirconate.

3. A method of carrying out x-ray examination of the gastrointestinal tract of a patient, said method comprises the oral or rectal administration to the patient an x-ray contrast composition designed for depositing a thin, flexible film membrane onto the mucosal lining of the nutrient absorbing inner surface of the intestine of a patient to form a barrier between said nutrient absorbing inner surface and the content of said intestine, said flexible film membrane to remain bound to said mucosal lining until eliminated by normal cell turnover comprising based on w/w:
   (a) of from about 0.001 to about 25% of a polymeric material capable of forming a film membrane on the gastrointestinal tract in the pH range of from about 5 to about 8, said the polymeric material being selected from the group consisting of:
   dermatan sulfate.
   hepatosulfate,
   hyabromic acid.
   heparin, chitin, and
ethylene oxide;
(b) of from about 0.1 to about 20% of a divalent cation to potentiate the binding of the flexible film membrane to the mucosal lining selected from the group consisting of $Ca^{++}$, $Mg^{++}$, $Zn^{++}$ and $Ba^{++}$;
(c) of from about 5 to about 95% of a barium salt in a liquid pharmaceutically acceptable carrier comprising a surfactant selected from the group consisting of
cetyltrimethyl ammonium bromide,
dodecyl ammonium bromide,
sodium lauryl sulfate,
sodium heptadecyl sulfate,
alkyl benzene sulfonic acid,
carboxylic esters,
carboxylic amides,
ethoxylated alkylphenols,
ethoxylated aliphatic alcohols,
polyoxyethylene alkyl ethers
polyoxyethylene sorbitan fatty acid esters; and
zwitterionic surfactants; and
exposing the gastrointestinal tract containing said x-ray contrast composition to x-rays to form an x-ray image pattern corresponding to the presence of said x-ray contrast composition, and visualizing said image pattern.

4. The method of claim 3 wherein said barium salt is selected from the group consisting of barium sulfate, barium hexaboride, barium chromite, barium fluogallate, barium tri-ortho phosphate, barium metasilicate, barium titanate, and barium zirconate.

* * * * *